United States Patent [19]

Vletter

[11] Patent Number: Plant 7,150

[45] Date of Patent: Feb. 13, 1990

[54] *ERYNGIUM PLANUM* PLANT NAMED SILVER STONE

[75] Inventor: Floris Vletter, Rijnsburg, Netherlands

[73] Assignee: de Vennootschap Onder Firma Gebr, Vletter & J.A. Den Haan, Netherlands

[21] Appl. No.: 260,731

[22] Filed: Oct. 21, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A distinct cultivar of *Eryngium planum* named Silver Stone, characterized by its large growth habit and rosette form, large and strong peduncles, and ellipsoid shaped flowers which are a distinctive greyish green in color.

2 Drawing Sheets

The present invention comprises a new and distinct cultivar of *Eryngium planum*, commonly called sea holly, known by the cultivar name Silver Stone.

Silver Stone originated from a hybridization made by the inventor Floris Vletter in a controlled breeding program in Rijnsburg, the Netherlands in 1982. The female, or seed, parent of Silver Stone was a cultivar designated F 80-1, as was the male, or pollen, parent. Silver Stone was discovered and selected as one flowering plant within the progeny of the stated parentage by the inventor on July 2, 1984 in a controlled environment in Rijnsburg, the Netherlands.

The first act of asexual reproduction of Silver Stone was accomplished when root cuttings were taken from the initial selection of July 30, 1984 in a controlled environment in Rijnsburg, the Netherlands under the supervision of the inventor. Horticultural examination of selected units, initiated on Sept. 11, 1986, has demonstrated that the combination of characteristics as herein disclosed for Silver Stone are firmly fixed and are retained through successive generations of asexual reproduction.

Silver Stone has not been observed under all possible environmental conditions. The phenotype may vary considerably with variations in environment such as temperature, light intensity and day length. The following observations, measurements and comparisons describe plants grown in Wageningen, the Netherlands under outside conditions which approximate those generally used in commerical practice. Color references are made to The Royal Horticultural Society Colour Chart.

The accompanying photographic drawings show a typical specimen plant of the new cultivar, with colors being as true as possible for color illustrations of this type.

Photographic Sheet 1 is a perspective view of mature plants of the variety.

Photographic Sheet 2 shows enlarged flower heads and connected peduncles of the variety.

The following traits have been repeatedly observed and are determined to be basic characteristics of Silver Stone, which in combination distinguish this *Eryngium planum* as a new and distinct cultivar:

1. Relatively large and tall plant, with dense rosette form.

2. Large and strong peduncles, branching out and formed with secondary and tertiary branches.

3. Almost ellipsoid shaped flowers, which are a distinguishing greyish green in color.

Plant:

*Form.*—Relatively large.

*Size.*—About 95 cm tall.

*Growth habit.*—Rosette is dense, and plant has large peduncles.

*Blooming habit.*—Branching flower heads.

Leaves:

*Size.*—Rosette leaves about 14 cm long with petioles of about 12 cm.

*Color.*—Dark green and dull-glossy.

*Quantity.*—Approximately 25.

*Shape.*—Almost elliptical, crenate, with leaf margin slightly pricked.

Peduncle:

*Size.*—From about 25 cm upwards, branching out somewhat wider and then with secondary and tertiary branches.

*Color.*—R.H.S. 194 A-B with much lighter vertical stripes.

*Stem leaves.*—Stem leaves sessile, leaf blades at the base of the peduncle more or less similar to those of the rosette leaves, upwards along the peduncle with deeper incisions and the palmately parted and very sharply pricked.

Flowers:

*Size.*—Medium sized the actual flowers size being 1.7 centimeters in height with a width of 1.5 centimeters. The number of flowers per stalk depends on the thickness of the roots, and varies from 40 to 100 flowers.

*Form.*—Almost ellipsoid, involucral leaves long and narrow, with a much lighter midrib.

*Color.*—Mature heads are a combination of colors not susceptible to color value identification. The heads appear greyish green overall, with green sepals and generally white petals and styles 191A-B in color.

Propagation: The new cultivar is reproduced through successive breeding generations by root cuttings.

I claim:

1. A new and distinct cultivar of *Eryngium planum* named Silver Stone, as illustrated and described.

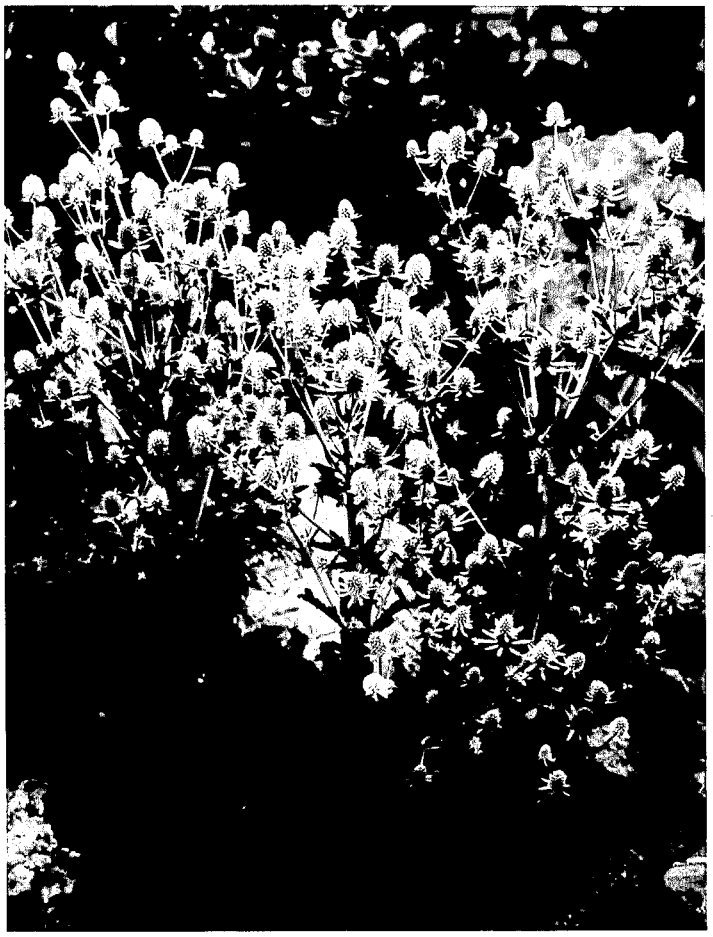

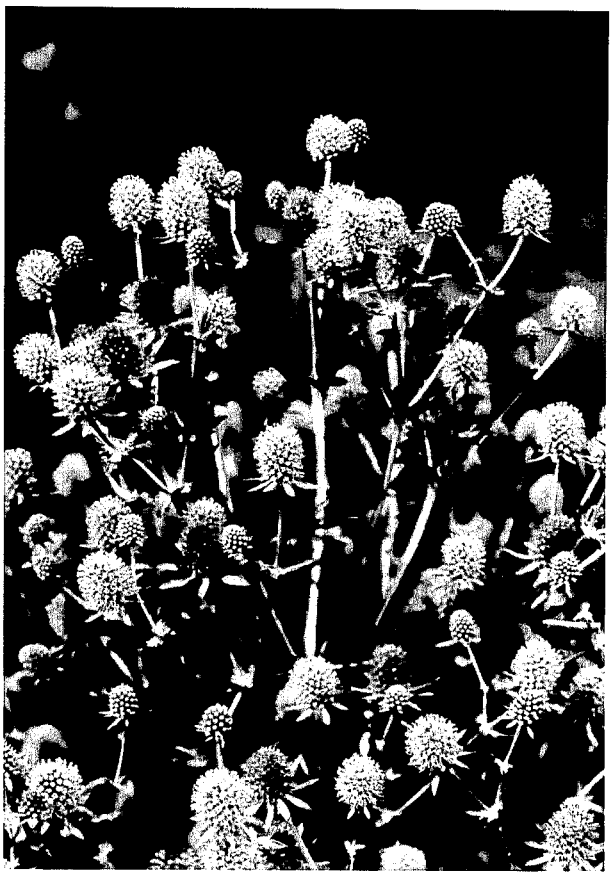

* * * * *